United States Patent [19]

Lannert et al.

[11] Patent Number: 4,704,465

[45] Date of Patent: Nov. 3, 1987

[54] PROCESS FOR PREPARING ETHYLENEDIAMINETETRAACETONITRILE

[75] Inventors: Kent P. Lannert, Freeburg, Ill.; Sum-Muk Lee, Ballwin, Mo.

[73] Assignee: Monsanto Company, St. Louis, Mo.

[21] Appl. No.: 800,856

[22] Filed: Nov. 22, 1985

[51] Int. Cl.$^4$ ........................................ C07C 120/00
[52] U.S. Cl. .................................................. 558/346
[58] Field of Search ........................................ 558/346

[56] References Cited

U.S. PATENT DOCUMENTS

| | | | |
|---|---|---|---|
| 2,855,428 | 10/1958 | Singer et al. | 558/346 |
| 3,061,628 | 10/1962 | Singer et al. | 548/346 |
| 3,424,783 | 1/1969 | Harper et al. | 558/346 |
| 4,478,759 | 10/1984 | Distler et al. | 558/346 |
| 4,560,516 | 12/1985 | Singer | 558/346 |

OTHER PUBLICATIONS

Krussig, Macromol. Chem. 17, pp. 77–130 (1956).
Bischoff, Der. Dtsch. Chem. GES, 31, pp. 3248–3257 and 3259–3260 (1898).
Bischoff, et al., Der Dtsch. Chem. GES, 36, pp. 35–40 (1903).

Primary Examiner—Joseph Paul Brust
Attorney, Agent, or Firm—R. C. Loyer; A. H. Cole

[57] ABSTRACT

A process for preparing an ethylenediamine intermediate for the production of an ethylenediaminetetraacetonitrile. Formaldehyde is combined with ethylenediamine at a mole ratio of 1 to 2 respectively wherein the molar ratio of ethylenediamine to formaldehyde in the reaction mixture at least 0.48 or greater.

9 Claims, No Drawings

PROCESS FOR PREPARING ETHYLENEDIAMINETETRAACETONITRILE

This invention relates to a process for providing an improved reaction product obtained by the reaction of an alkyleneamine and formaldehyde. More particularly, this invention relates to a process whereby increased conversion of alkyleneamineformaldehyde reaction product to the corresponding tetraacetonitrile is obtained. Such nitriles are precursors of chelating agents which are formed by the hydrolysis of the nitrile to the corresponding acid or salt form.

The reaction of an amine or ammonia and formaldehyde has long been known. The reaction of aliphatic diamines with formaldehyde has been reported by Hans Krussig in *Macromol Chem.*, 17, 77–130 (1956). His work was preceded by C. A. Bischoff, Studien über Verkettungen. SSSV. Formaldehyd und zweisäaurige Basen, *Der. dtsch. chem. GES.*, 31, 3248–3260 (1898) as well as by C. A. Bischoff and F. Reinfeld, Formaldehyd-derivate aliphatischer Basen, *Der. dtsch. chem. GES.*, 36, 35–40 (1903). The above-mentioned publications disclose numerous procedures for reacting many different amines and formaldehyde. Krussig discloses numerous reactions involving aliphatic amines and formaldehyde at various mole ratios.

Amine-formaldehyde reaction products are employed as intermediates to produce amino nitriles and corresponding acid salts that are widely known to have complexing ability with metal ions in water solution. The amino acid salts, such as trisodium nitrilotriacetate or tetrasodium ethlyenediaminetetraacetate are incorporated into detergent and water treating formulations for household and industrial use wherein the complexing ability of the salts results in sequestration of solubilized metal ions in the wash water.

In recent years there has been a need to reduce cost of manufacturing the above-mentioned amino acid salts and to reduce waste. There has now been found a process for preparing amine-formaldehyde reaction products which result in increased yields of amino nitriles.

SUMMARY OF THE INVENTION

In accordance with this invention there is provided a process for preparing an ethylenediamineformaldehyde reaction product by reacting ethylenediamine with formaldehyde wherein the molar ratio of ethylenediamine to formaldehyde in the reaction mixture is at least about 0.48 or above. It is preferred that the molar ratio of ethylenediamine to formaldehyde be slightly in excess of about 0.5. The reaction product obtained in accordance with this invention has been found to provide increased yields of ethylenediaminetetraacetonitrile when the reaction product is combined with a liquid phase reaction medium comprising hydrogen cyanide, water, sulfuric acid and formaldehyde.

In one embodiment of this invention the ethylenediamine is placed in a reaction zone and formaldehyde is added to the amine. Such procedure ensures that during most of the reaction time a stoichiometric excess of ethylenediamine is present in the reaction mixture most importantly at the early stages of the reaction.

DETAILED DESCRIPTION OF THE INVENTION

The chemical structure of the reaction product of ethylenediamine and formaldehyde is not fully understood. Although referred to herein as octamethylenetetramine (OMTA) the actual structure and identity of the reaction product and related materials produced by the reaction remain essentially undefined. The reaction is generally represented as follows:

$$2H_2NCH_2CH_2NH_2 + 4CH_2O \rightarrow OMTA + 4H_2O \qquad I$$

Reaction I readily occurs when ethylenediamine and an aqueous solution of formaldehyde are mixed together. Formaldehyde is typically available commercially in aqueous solution at concentrations such as from about 20% to about 56%. Usually it is convenient to employ a 50% by weight aqueous solution of formaldehyde in the process of this invention. Other commercially available material contains about 37% formaldehyde in aqueous solution. These solutions are commonly known as formalin.

Since ethylenediamine remains liquid above 11° C. and is easily handled in that form, it is normally maintained in the liquid form and added to a reaction vessel which, in the process of this invention is typically equipped with temperature regulating means. Ethylenediamine reacts exothermically with formaldehyde and is typically carried out under a nitrogen atmosphere.

The reaction temperature is controlled by cooling and is typically in the range of from about 15° C. to about 65° C. and preferably in the range of from about 40° C. to about 60° C. with an average temperature of about 60° C. preferred. A jacketed reaction vessel is typically employed and temperature control is aided by employing agitation of the reaction mixture. One preferred means to agitate the reaction mixture is the recycle of the mixture through the reactor. After complete addition of the reactant the temperature may be allowed to decrease to a convenient temperature. The reaction product is very soluble in water and is easily removed from the reactor.

In one preferred embodiment a continuous process is employed whereby stoichiometric amounts of ethylenediamine and formaldehyde in aqueous solution are simultaneously introduced into a suitable reaction vessel near the bottom or at least below the surface of the reaction mixture. The reaction product is continuously withdrawn from the reaction vessel mixture. In this embodiment the reaction vessel is suited to enable a brief sojourn of the reactants from the point of entry into the reaction vessel to the exit point of the product. The reaction between ethylenediamine and formaldehyde is nearly instantaneous necessitating only a brief hold period in the reaction vessel to accomplish complete reaction.

In a more preferred embodiment the above described continuous process further includes the step of simultaneously adding to a second reaction vessel ethylenediamine-formaldehyde reaction product and hydrogen cyanide in liquid form to a heel comprising hydrogen cyanide, water, sulfuric acid and formaldehyde whereby ethylenediaminetetraacetonitrile is formed under known conditions.

It has been discovered that the ethylenediamine-formaldehyde reaction product obtained in accordance with this invention provides increased yield of the above mentioned nitrile. The increased yield of nitrile is obtained by means of either batch or continuous process in production of the ethylenediamine-formaldehyde reaction product in accordance with this invention. The reaction conditions employed to produce the ethylenediaminetetraacetonitrile are similar to prior art processes with the exception of the modification of the process of making the ethylenediamine-formaldehyde reaction product provided in accordance with this invention.

Particularly in a batch process the pH of the reaction mixture is maintained at a higher level than processes in the prior art wherein ethylenediamine is added to formaldehyde. The pH of the reaction mixture is typically in the range of above about 9. The more basic amine reactant maintains the relatively higher pH whereas formaldehyde is consumed upon addition.

In accordance with this invention it has been found that a convenient means for combining ethylenediamine and formaldehyde is to introduce ethylenediamine into the reaction vessel first and then add an aqueous solution of formaldehyde to the ethylenediamine. In this manner there is provided a stoichiometric excess of ethylenediamine in the reaction vessel throughout the addition of all or most of the formaldehyde solution. In this embodiment the reaction product will contain unreacted or incompletely reacted ethylenediamine. The amount of stoichiometric excess of ethylenediamine is in the range of from about 0.01 mole percent to about 10 mole percent and preferably in the range of from about 0.1 mole percent to about 2 mole percent.

Because the reaction product of ethylenediamine and formaldehyde is employed as an intermediate and will be added to a reaction mixture including further formaldehyde, any excess ethylenediamine in the reaction product is not lost but will be reacted with an appropriate excess of formaldehyde in the next reaction step as will be noted below.

As noted above, the reaction product of ethylenediamine and formaldehyde is employed as an intermediate to prepare ethylenediaminetetraacetonitrile (EDTN). EDTN is well known in the prior art and the advantages of the present invention are obtained by employing the ethylenediamine-formaldehyde reaction product prepared in accordance with this invention. It has been found that the ethylenediamine-formaldehyde reaction product prepared in accordance with the process of this invention provides increased yield of EDTN over that obtained with the ethylenediamine-formaldehyde reaction product provided by processes known in the prior art.

In one method whereby EDTN is produced, the combination of the ethylenediamine-formaldehyde reaction product represented by OMTA and liquid hydrogen cyanide are added to a reaction vessel containing a heel comprising hydrogen cyanide, water, sulfuric acid and formaldehyde. The reaction is represented by the following equation:

OMTA+4 H$_2$O+8HCN→2[(NCCH$_2$)$_2$NCH$_2$—]$_2$+4H$_2$O

At the end of the reaction, usually after about 1½ hours, a slurry of EDTN in water is obtained. The nitrile is only slightly soluble in water such that cooling the reaction mixture allows simple separation of the product by means of filtration. The crystals of EDTN, are employed to provide the tetrasodium salt of ethylenediaminetetraacetic acid by known means.

The surprising advantage obtained by producing the ethylenediamine-formaldehyde reaction product in accordance with this invention is demonstrated by the following non-limiting examples.

EXAMPLE I (Prior Art)

A jacketed 2 L glass reactor was charged with 892.3 g of 50.33% formalin solution (14.95 moles) which had been maintained at 50°–60° C. to prevent paraformaldehyde formation. Ethylenediamine, 452.1 g assayed at 99.4% (7.477 moles), was added at such a rate that the temperature could be maintained at 50°–60° C. by circulating water through the jacket. At the end of the ethylenediamine addition the reaction mixture was cooled to room temperature. The reaction resulted in an aqueous solution of ethylenediamine-formaldehyde reaction product.

The aqueous solution was employed to produce ethylenediaminetetraacetonitrile (EDTN) by first preparing a heel in a reactor equipped with a heating means, an agitator and a reflux condenser as follows: 31.43 g of H$_2$O, 93.51 g of 37.0% formalin (1.153 moles), 4.98 g of 95% H$_2$SO$_4$ and 13.4 ml 98% HCN (d =0.715 g/ml) (0.348 mole). To this was simultaneously added 98.89 g of the above ethylenediamine-formaldehyde reaction product aqueous solution (0.2768 moles) and 75.6 ml of 98% HCN (1.963 moles). The HCN was added over a period of 105 minutes and the ethylenediamine-formaldehyde reaction product solution was added over a period of 113 minutes. The temperature of the reaction mixture during most of the addition of ethylenediamine-formaldehyde reaction product solution was 60°–70° C. After cooling the reaction mixture, EDTN was collected on a filter, washed and dried. The yield of EDTN was 102.94 g or 86.1% based on the ethylenediamine equivalent in the ethylenediamine-formaldehyde reaction product.

EXAMPLE II

To the same apparatus described in Example I, 450.4 g of ethylenediamine (7.449 mole) was charged. To this was added 889.0 g of 50.33% formalin solution (14.90 mole). The temperature quickly rose to 60° C. and was maintained at 50°–60° C. throughout the remainder of the formalin addition by circulating water through the jacket. At the end of the ethylenediamine addition the reaction mixture was cooled to room temperature. There was thus produced an ethylenediamine-formaldehyde reaction product in water solution.

This solution produced as described above was used to make EDTN by the same procedure as described in Example I. The amounts contained in the heel were 31.36 g of H$_2$O, 4.98 g of 95% H$_2$SO$_4$, 101.68 g of 37.0% formalin (1.253 moles), 13.4 ml 98% HCN (0.348 mole). To this, 98.79 g (0.2776 mole) of the ethylenediamine-formaldehyde reaction product solution from above and 75.6 ml 98% HCN (1.963 moles) were added simultaneously on the same schedule as in Example I. The temperature profile of the reaction was similar to Example I. The yield of EDTN was 115.26 g or 96.1% based on the ethylenediamine equivalent in the ethylenediamine-formaldehyde reaction product.

Although the invention has been described in terms of specified embodiments which are set forth in considerable detail, it should be understood that this is by way of illustration only and that the invention is not necessarily limited thereto since alternative embodiments in operating techniques will become apparent to those skilled in the art in view of the present disclosure. Accordingly, modifications are contemplated which can be made without departing from the spirit of the described invention.

What is claimed is:

1. A process for preparing ethylenediaminetetraacetonitrile which comprises:
   a. reacting ethylenediamine with formaldehyde wherein the formaldehyde is added to the ethylenediamine in a reaction vessel and wherein the molar ratio of ethylenediamine to formaldehyde in the reaction mixture is at least about 0.48 to form a reaction product and, thereafter,
   b. simultaneously adding said reaction product and liquid hydrogen cyanide to a heel comprising hydrogen cyanide, water, sulfuric acid and formaldehyde whereby ethylenediaminetetraacetonitrile is formed.

2. The process of claim 1 wherein the amount of sulfuric acid is sufficient to maintain the pH of the reaction mixture below about 1.

3. The process of claim 1 wherein the amount of hydrogen cyanide in the heel is from about 10% to about 25% of the total amount.

4. The process of claim 1 wherein the temperature of the reaction zone in step a. is in the range of from about 15° C. to about 65° C.

5. The process of claim 1 wherein the pH of the reaction mixture in step a. is above about 9.

6. The process of claim 1 wherein the amount of ethylenediamine is in stoichiometric excess.

7. The process of claim 1 wherein the molar ratio of ethylenediamine to formaldehyde is in excess of 0.5.

8. The process of claim 6 wherein the stoichiometric excess is in the range of from about 0.01 mole percent to about 10 mole percent by weight.

9. The process of claim 1 wherein the concentration of the aqueous formaldehyde solution is in the range of from about 20% to about 56%, by weight.

* * * * *

UNITED STATES PATENT AND TRADEMARK OFFICE
CERTIFICATE OF CORRECTION

PATENT NO. : 4,704,465
DATED : November 3, 1987
INVENTOR(S) : K. P. Lannert et al It is certified that error appears in the above—identified patent and that said Letters Patent is hereby corrected as shown below:

Column 3, line 55, delete

"OMTA + 4-
$H_2O$ + 8HCN -----> $2[(NCCH_2)_2 NCH_2-]_2$ + $4H_2O$"

and insert therefor

--OMTA + $4CH_2O$ + 8HCN -----> $2[(NCCH_2)_2 NCH_2-]_2$ + $4H_2O$--

Signed and Sealed this

Twelfth Day of April, 1988

Attest:

DONALD J. QUIGG

Attesting Officer

Commissioner of Patents and Trademarks